United States Patent [19]

Dolman et al.

[11] Patent Number: 4,994,485
[45] Date of Patent: Feb. 19, 1991

[54] THIO COMPOUNDS HAVING FUNGICIDAL ACTIVITY

[75] Inventors: Hendrik Dolman; Johannes Kuipers, both of Weesp, Netherlands

[73] Assignee: Duphar International Research B.V., Weesp, Netherlands

[21] Appl. No.: 566,868

[22] Filed: Aug. 14, 1990

Related U.S. Application Data

[63] Continuation of Ser. No. 395,220, Aug. 17, 1989, abandoned, which is a continuation of Ser. No. 175,601, Mar. 29, 1988, abandoned, which is a continuation of Ser. No. 14,596, Feb. 13, 1987, abandoned.

[30] Foreign Application Priority Data

Feb. 19, 1986 [NL] Netherlands .................. 8600416
May 22, 1986 [NL] Netherlands .................. 8601296

[51] Int. Cl.$^5$ .................. A01N 43/06; C07D 333/38
[52] U.S. Cl. ........................ 514/445; 549/61
[58] Field of Search .................. 514/445; 549/61

[56] References Cited

U.S. PATENT DOCUMENTS 4,451,660 5/1984 Dolman et al. .................. 549/63

FOREIGN PATENT DOCUMENTS 0739270 9/1968 Belgium .................. 549/61

Primary Examiner—Alan Siegel
Attorney, Agent, or Firm—Stevens, Davis, Miller & Mosher

[57] ABSTRACT

The invention relates to new thio compounds of the general formula

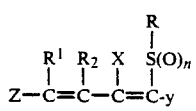

wherein

R is an alkyl group substituted or not substituted with halogen and having 1–12 carbon atoms, an alkenyl or alkynyl group having 2–4 carbon atoms, an alkadienyl group having 3 or 4 carbon atoms or a substituted or unsubstituted phenyl or phenyl($C_1$–$C_4$)alkyl group;

$R_1$ is a cyano group, a formyl group, an alkylcarbonyl or alkoxycarbonyl group substituted or unsubstituted with halogen and having 2–5 carbon atoms, a substituted or unsubstituted benzoyl group, or an alkylsulphonyl group having 1–4 carbon atoms;

$R_2$ is a hydrogen atom, a halogen atom, an amino group unsubstituted or substituted with one or two groups selected from $C_1$–$C_4$ alkyl and $C_2$–$C_5$ alkylcarbonyl, an amino group forming part of a heterocyclic ring which may comprise 1 or 2 additional heteroatoms selected from N, O and S, an alkyl or alkoxy group having 1–4 carbon atoms and optionally substituted with $C_2$–$C_5$ alkylcarbonyl, or a substituted or unsubstituted phenyl, phenoxy or phenylthio group;

or wherein $R_1$ and $R_2$, together with the vinylene group to which they are bound, constitute a substituted or unsubstituted phenyl group;

X is a cyano group or a formyl group;

n is 1 or 2;

Y is an alkylthio group having 1–4 carbon atoms; and

Z is a hydrogen atom, a halogen atom, a nitro group, or an alkyl or alkoxy group having 1–4 carbon atoms and optionally substituted with halogen;

or wherein Y and Z together constitute a sulphur atom; with the proviso that, when Y and Z do not together constitute a sulphur atom, $R_1$ and $R_2$, together with the vinylene group to which they are bound, constitute a substituted or unsubstituted phenyl group.

The new compounds show a fungicidal and/or bactericidal activity and may be used in particular against plantpathogenic seed fungi and soil fungi and/or bacteria.

7 Claims, No Drawings

THIO COMPOUNDS HAVING FUNGICIDAL ACTIVITY

This application is a continuation of application Ser. No. 395,220, filed Aug. 17, 1989, which in turn is a continuation of application Ser. No. 175,601, filed Mar. 29, 1988, which in turn is a continuation of application Ser. No. 014,596, filed Feb. 13, 1987, now abandoned.

The invention relates to new thio compounds as well as to a method of preparing the said compounds. The invention furthermore relates to fungicidal and/or bactericidal compositions, and in particular to compositions for the treatment of soil or seed against phytophagous micro-organisms, which compositions comprise the new compounds as the active substances, and to the use of the said compositions in agriculture and horticulture.

Nitrothiazoles having fungicidal activity, for example, for the treatment of seeds, are known from German Offenlegungoschrift No. 2,627,328. A compound described in this Application is 2-methylsulphinyl-4-methyl-5-nitrothiazole. However, in practice this compound has proved to be insufficiently active, as will become apparent from the examples.

Nitrothiophenes having fungicidal activity, intended in particular for the treatment of seed or soil against phytophagous micro-organisms, are disclosed in United States Pat. No. 4,451,660. Compounds described in this Patent Specification are 2-methylsulphinyl-3-nitrothiophene and 2-ethylsulphinyl-3-nitro-5-acetylthiophene. It has been found, however, that the activity of these compounds also leaves to be desired in practice. Moreover, the compounds show an undesired toxicity with respect to warm-blooded living beings.

It is the object of the invention to provide new thio compounds having an improved fungicidal and/or bactericidal activity, in particular against plant pathogenic seed fungi and soil fungi and/or bacteria, and having a decreased toxicity with respect to warm-blooded living beings. This object can be achieved by means of new thio compounds which are characterized according to the invention by the general formula

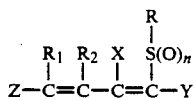

(I)

wherein

R is an alkyl group substituted or not substituted with halogen and having 1–12 carbon atoms, an alkenyl or alkynyl group having 2–4 carbon atoms, an alkadienyl group having 3 or 4 carbon atoms, or a substituted or unsubstituted phenyl or phenyl($C_1$–$C_4$)alkyl group;

$R_1$ is a cyano group, a formyl group, an alkylcarbonyl or alkoxycarbonyl group substituted or not substituted with halogen and having 2–5 carbon atoms, a substituted or unsubstituted benzoyl group, or an alkylsulphonyl group having 1–4 carbon atoms;

$R_2$ is a hydrogen atom, a halogen atom, an amino group unsubstituted or substituted with one or two groups selected from $C_1$–$C_4$ alkyl and $C_2$–$C_5$ alkylcarbonyl, an amino group forming part of a heterocyclic ring which may comprise 1 or 2 additional heteroatoms selected from N, O and S, an alkyl or alkoxy group having 1–4 carbon atoms and optionally substituted with halogen or $C_2$–$C_5$ alkylcarbonyl, or a substituted or unsubstituted (hetero)aryl, (hetero)aryloxy or (hetero)arylthio group;

or wherein $R_1$ and $R_2$, together with the vinylene group to which they are bound, constitute a substituted or unsubstituted phenyl group;

X is a cyano group or a formyl group;

n is 1 or 2;

Y is an alkylthio group having 1–4 carbon atoms; and

Z is a hydrogen atom, a halogen atom, a nitro group, or an alkyl or alkoxy group having 1–4 carbon atoms and optionally substituted with halogen;

or wherein Y and Z together constitute a sulphur atom; with the proviso that, when Y and Z do not together constitute a sulphur atom, $R_1$ and $R_2$, together with the vinylene group to which they are bound, constitute a substituted or unsubstituted phenyl group.

Where a substituted aryl or phenyl group is mentioned hereinbefore, the aryl or phenyl group may be substituted with a substituent or with more equal or different substituents. Examples of suitable substituents are halogen, nitro, cyano, $C_1$–$C_4$ alkyl, $C_1$–$C_4$ haloalkyl, $C_1$–$C_4$ alkoxy, $C_1$–$C_4$ haloalkoxy and $C_1$–$C_4$ alkylsulphonyl. Suitable examples of (hetero)aryl, (hetero)aryloxy and heteroarylthio groups are phenyl, phenoxy, phenylthio, quinolyloxy, pyridylthio, thienyloxy and thiazolylthio.

Of the above-mentioned compounds are to be preferred thio compounds of the general formula

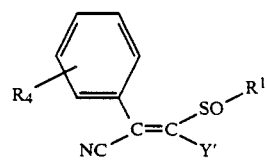

(II)

wherein

R' is an alkyl group having 1–4 carbon atoms,

Y is an alkylthio group having 1–4 carbon atoms, and $R_4$ is a hydrogen atom or represents one or more substituents selected from the group consisting of halogen, nitro, $C_1$–$C_4$ alkyl, $C_1$–$C_4$ alkoxy, $C_1$–$C_4$ haloalkyl and $C_1$–$C_4$ haloalkoxy;

as well as thiophenes of the general formula

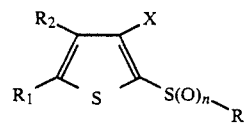

(III)

wherein R, $R_1$, $R_2$, X and n have the above meanings.

Compounds of the former group, i e. of the general formula II, may occur in two stereoisomers, namely in the Z-form (cis-form) and the E-form (trans-form). Of course, mixtures of these steroisomers in any ratio are possible. If desired, these steroisomers may be separated from each other by means of techniques known for this purpose. The activity can be influenced by the steric configuration.

Of the latter group of compounds, i.e. compounds of the general formula III, are to be preferred compounds of the general formula

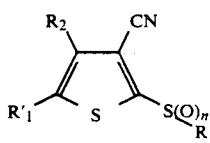

wherein $R_1'$ is a cyano group, a formyl group, an alkylcarbonyl group having 2-5 carbon atoms, or a benzoyl group which may be substituted with one or more substituents selected from the group consisting of halogen, nitro, $C_1$-$C_4$ alkyl, $C_1$-$C_4$ alkoxy, $C_1$-$C_4$ haloalkyl and $C_1$-$C_4$ haloalkoxy, and n, R and $R_2$ have the above meanings, or wherein $R_1'$ and $R_2$, together with the vinylene group to which they are bound, constitute a phenyl group which optionally may be substituted with one or more substituents selected from the group consisting of halogen, nitro, $C_1$-$C_4$ alkyl, $C_1$-$C_4$ alkoxy, $C_1$-$C_4$ haloalkyl and $C_1$-$C_4$ haloalkoxy.

Of the last-mentioned compounds prove to be excellently suitable as fungicides and/or bactericides compounds of the general formula

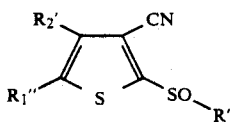

wherein $R'$ is an alkyl group having 1-4 carbon atoms, $R_1''$ is a cyano group, a formyl group, an acetyl group, an unsubstituted benzoyl group or a benzoyl group substituted with one or two halogen atoms, and $R_2'$ is a hydrogen atom, a halogen atom, an alkyl group or alkoxy group having 1 or 2 carbon atoms, or an amino group substituted or not substituted with a methyl group.

Examples of new thio compounds according to the invention are:

(1) 2-methylsulphinyl-3-cyano-5-acetylthiophene,
(2) 2-methylsulphinyl-3-cyano-4-chloro-5-acetylthiophene,
(3) 2-methylsulphinyl-3,5-dicyano-4-chlorothiophene,
(4) 2-methylsulphinyl-3,5-dicyanothiophene,
(5) 2-ethylsulphinyl-3-cyano-4-chloro-5-acetylthiophene,
(6) 2-methylsulphinyl 3-cyano-4-(4-chlorophenyl)-5-acetylthiophene,
(7) 2-ethylsulphinyl-3,5-dicyano-4-chlorothiophene,
(8) 2-ethylsulphinyl-3,5-dicyanothiophene,
(9) 2-ethylsulphinyl-3-cyano-5-acetylthiophene,
(10) 2-ethylsulphinyl-3-cyano-4-amino-5-acetylthiophene,
(11) 2-methylsulphinyl-3-cyano-4-chloro-benzothiophene,
(12) 2-methylsulphinyl-3,5-dicyano-4-methoxythiophene,
(13) 2-ethylsulphinyl-3,5-dicyano-4-methoxythiophene,
(14) 2-ethylsulphinyl-3,5-dicyano-4-ethoxythiophene,
(15) α-cyano-β-merhylsulphinyl-β-methylthio-3,4-dichloro-styrene,
(16) 2-ethylsulphonyl-3,5-dicyanothiophene,
(17) 2-ethylsulphinyl-3-cyano-4-N-methylamino-5-acetylthiophene,
(18) 2-ethylsulphonyl-3-cyano-4-chloro-5-acetylthiophene,
(19) α-cyanoβ-methylsulphinyl-β-methylthio-4-chlorostyrene,
(20) 2-ethylsulphinyl-3-cyano 6-chloro-benzothiophene,
(21) 2-ethylsulphonyl-3-cyano-5-acetylthiophene,
(22) 2-ethylsulphonyl-3,5 dicyano-4-chlorothiophene,
(23) 2-ethylsulphinyl-3-cyano-4-methoxy-5-acetylthiophene,
(24) 2-propargylsulphinyl-3,5-dicyano-4-methoxythiophene,
(25) 2-methylsulphinyl-3-cyano-4-methoxy-5-acetylthiophene,
(26) 2-methylsulphinyl-3-cyano-4-(4-chlorophenyl)-5-formylthiophene,
(27) 2-ethylsulphinyl-3-cyano-6-nitro-benzothiophene,
(28) 2-methylsulphinyl-3-cyano-5-formylthiophene,
(29) 2-methylsulphinyl-3-cyano-4-amino-5-ethoxycarbonylthiophene,
(30) 2-methylsulphinyl-3-cyano-5-benzoylthiophane,
(31) 2-methylsulphinyl-3-cyano-4-chloro 5-benzoylthiophene,
(32) 2-phenylsulphinyl-3,5-dicyanothiophene,
(33) 2-n-propylsulphinyl-3,5-dicyano-4-chlorothiophene,
(34) 2-n-hexylsulphinyl-3,5-dicyano-4-chlorothiophene,
(35) 2-methylsulphinyl-3,5-dicyano-4-(4-chlorophenyl)-thiophene,
(36) 2-n-octylsulphinyl-3,5-dicyano-4-chlorothiophene,
(37) 2-ethylsulphinyl 3-cyano-4-chloro-5-ethoxycarbonylthiophene,
(38) 2-n-hexylsulphinyl-3,5-dicyano-4-aminothiophene,
(39) 2-n-butylsulphinyl 3-cyano-4-chloro-5-acetylthiophene,
(40) 2-n-propylsulphinyl 3,5-dicyanothiophene,
(41) 2-n-butylsulphinyl-3,5-dicyano 4-methoxythiophene,
(42) 2-methylsulphinyl-3-cyano-4-chloro-5-(4-chlorobenzoyl) thiophene,
(43) 2-n-butylsulphinyl -3,5-dicyano-4-chlorothiophene,
(44) 2-n-butylsulphinyl-3-cyano-5-acetylthiophene,
(45) 2-phenylsulphonyl-3,5-dicyanothiophene,
(46) 2-ethylsulphinyl-3,5-dicyano-4-aminothiophene,
(47) 2-ethylsulphinyl-3-cyano-5-(4-chlorobenzoyl)thiophene,
(48) 2-methylsulphinyl-3-cyano-4-amino-5-formylthiophene,
(49) 2-ethylsulphinyl-3-cyano-4-amino-5-formylthiophene,
(50) 2-ethylsulphinyl-3-cyano-4-chloro-5-formylthiophene,
(51) 2-methylsulphinyl-3-cyano-5-benzoylthiophene,
(52) 2-methylsulphinyl-3-cyano-5-(4-chlorobenzoyl)thiophene,
(53) α-cyano-β-ethylsulphinyl-β-ethylthio-4-chlorostyrene,
(54) 2-ethylsulphinyl-3,5-dicyano-4-(N-acetyl-N-methylamino)thiophene,
(55) 2-n-propylsulphinyl-3,5-dicyano-4-methoxythiophene,
(56) 2-ethylsulphinyl-3-cyano-4-methyl-5-formylthiophene,
(57) 2-n-propylsulphinyl-3-cyano-4-amino-5-acetylthiophene,
(58) 2-n-butylsulphinyl-3 cyano-4-amino-5-acetylthiophene,
(59) 2-methylsulphinyl-3-cyano-4-acetylmethoxy-5-acetylthiophene,

(60) 2-methylsulphinyl-3-cyano-5-methylsulphonylthiophene,
(61) 2-n-propylsulphinyl-3-cyano-4-cloro-5-acetylthiophene,
(62) 2-n-propylsulphinyl-3-cyano-4-methyl-5-acetylthiophene,
(63) 2-ethylsulphinyl-3,5-dicyano-4-methylthiophene,
(64) 2-ethylsulphinyl-3-cyano-5-benzoylthiophene,
(65) 2-ethylsulphinyl-3-cyano-4-amino-5-benzoylthiophene,
(66) 2 ethylsulphinyl-3-cyano-4-amino-5-(4-chlorobenzoyl)thiophene,
(67) 2-n-propylsulphinyl-3-cyano-4-amino-5-benzoylthiophene,
(68) 2-ethylsulphinyl-3,5-dicyano-4-(1,2,4-triazol-1-yl)thiophene,
(69) 2-ethylsulphinyl-3,5-dicyano-4-(imidazol-1-yl)thiophene,
(70) 2-methylsulphinyl-3,5-diformylthiophene,
(71) 2-ethylsulphinyl-3,5-dicyano-4-phenylthiophene,
(72) 2-ethylsulphinyl-3-cyano-4-chloro-5-(4-chlorobenzoyl)thiophene,
(73) 2-n-propylsulphinyl-3-cyano-5-(4-chlorobenzolyl)thiophene,
(74) 2-methylsulphinyl-3-cyano-4-methoxy-5-benzoylthiophene,
(75) 2-n-propylsulphinyl-3-cyano-4-methoxy-5-benzoylthiophene,
(76) 2-ethylsulphinyl-3-cyano-4-methoxy-5-(4-chlorobenzoyl)thiophene,
(77) 2-ethylsulphinyl-3-cyano-4-chloro-5-methylsulphonyl-thiophene,
(78) 2-benzylsulphinyl-3,5-dicyano-4-chlorothiophene,
(79) 2-n-butylsulphinyl-3,5-dicyano-4-bromothiophene,
(80) 2-n-butylsulphinyl-3,5-dicyanothiophane,
(81) 2-n-octylsulphinyl-3,5-dicyanothiophene,
(82) 2 phenylsulphinyl-3,5-dicyano-4-chlorothiophene,
(83) 2-ethylsulphinyl-3,5-diformyl-4-chlorothiophene,
(84) 2-ethylsulphonyl-3-cyano-4-chloro-5-methylsulphonylthiophene,
(85) 2-methylsulphinyl-3,5-dicyano-4-phenylthio-thiophene,
(86) 2-n-butylsulphinyl-3-cyano-4-bromo-5-acetylthiophene,
(87) 2-ethylsulphinyl-3-cyano-4-phenyl-5-acetylthiophene,
(88) 2-n-butylsulphinyl-3-cyano-4-amino-5-benzoylthiophene,
(89) 2-n-butylsulphonyl 3,5-dicyano-4-bromothiophene,
(90) 2-n-butylsulphinyl 3-cyano-5-benzoylthiophene,
(91) 2-ethylsulphinyl-3-cyano-4-methyl-5-benzoylthiophene,
(92) 2-ethylsulphinyl-3-cyano-4-chloro-5-benzoylthiophene,
(93) α-cyano-β-methylsulphinyl)-β-methylthio-styrene, E-isomer, and
(94) 2-ethylsulphinyl-3,5-dicyano-4-phenoxythiophene.

The new compounds according to the invention show an interesting fungicidal activity with respect to a wide spectrum of pathogenic fungi which may occur in agricultural and horticultural crops.

The compounds according to the invention may be used against so-called air-borne, soil-borne and seed-borne pathogens. Examples of air-borne pathogenic fungi are Uromyces phaseoli and Phytophthora infestans.

It has been found that the new compounds according to the invention are particularly active against soil-borne and seed-borne pathogenic micro-organisms, i.e. against phytophagous soil fungi ("soil-borne diseases"), for example, Pythium spp, (for example, Pythium ultimum and Pythium splendens) and Rhizoctonia solani, against phytophagous fungi which are seed-borne ("seed-borne diseases"), for example, Pyrenophora graminea on barley, Tilletia caries on wheat, Fusarium spp. (for example, Fusarium nivale and Fusarium culmorum) on wheat, Leptosphaeria nodorum on wheat and Ustilago spp. (for example, Ustilago avenae) on oats, and against phytophagous bacteria, for example, Erwinia carotovora.

Infections with phytophagous bacteria and/or fungi, e.g. phytophagous soil fungi or fungi which are seed-borne, can be prevented by treating the soil destined for planting or sowing, or, which will usually be preferred for economical reasons, the seed itself with a composition which comprises a new compound according to the invention. For practical applications the substances in accordance with the invention are processed to compositions. In such compositions the active substance is mixed with solid carrier material or dissolved or dispersed in liquid carrier material, if desired in combination with auxiliary substances, for example, emulsifiers, wetting agents, dispersing agents and stabilizers.

Examples of compositions according to the invention are aqueous solutions and dispersions, oily solutions and oily dispersions, solutions in organic solvents pastes, dusting powders, dispersing powders, miscible oils, granules and pellets.

Dispersible powders, pastes and miscible oils are compositions in concentrate form which are diluted prior to or during use. The solutions in organic solvents are mainly used in air application, namely when large areas are treated with a comparatively small quantity of composition. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/-suspension, if desired in the presence of a binder, on granular carrier material, for example porous granules (sand or ground marl), organic granules (for example, dried coffee grounds, cut tobacco stems and ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then to the desired particle size.

Dusting powders can be obtained by intimately mixing the active substance with an inert solid powdered carrier material, for example, talcum.

Dispersible powders are prepared by mixing 10 to 80 parts by weigt of a solid inert carrier, for example kaolin dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable solvents are, for example, xylene, toluene, petroleum distillates which are rich in aromatics, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily water-miscible liquid, for example, a glycol, or glycol ether, to which solution a dispersing agent and, if desired, a surface active substances has been added. When diluting with water shortly before or during spraying, an aqueous dispersion of the active substance is then obtained.

In addition to the above mentioned ingredients, the agents according to the invention may also contain other substances known for use in this type of agents. For example, a lubricant, for example, calcium stearate or magnesium stearate, may be added to a dispersible powder or a mixture to be granulated. "Adhesives", for example, polyvinylalcohol cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the invention. As a result of this the activity spectrum of the composition is widened and synergism may occur.

For use in such a combination composition are to be considered the following known insecticidal, acaricidal and fungicidal compounds.

Insecticides, for example:

1. organic chlorine compounds, for example: 6,7,8,9,10,10-hexachloro-1,5,5a,6,9,9a-hexahydro-6,9-methano-2,4,3-benzo[e]-dioxathiepine-3-oxide;

2. carbamates, for example: 2-dimethylamino-5,6-dimethylpyrimidin-4-yl dimethyl carbamate and 2-isopropoxyphenyl methylcarbamate;

3. di(m)ethylphosphates, for example: 2-chloro-2-diethylcarbamoyl-1-methylvinyl-,2-methoxycarbonyl 1-methylvinyl-,2-chloro-1-(2,4-dichlorophenyl)vinyl-, and 2-chloro-1-(2,4,5-trichlorophenyl)vinyl di(m)ethyl phosphate;

4. O,O-di(m)ethyl phosphorothioates, for example, O(S)-2-methylthioethyl-, S-2-ethylsulphinylethyl-,S-2-(1-methylcarbamoylethylthio)ethyl-, 0-4-bromo-2,5-dichloro-phenyl-, 0-3,5,6-trichloro-2-pyridyl-,0-2-isopropyl-6-methylpyrimidin-4-yl-, and 0-4-nitrophenyl 0,0-di(m)ethyl phosphorothioate;

5. O,O-di(m)ethyl phosphorodithioates, for example, S-methylcarbamoylmethyl-,S-2-ethylthioethyl-, S-(3,4-dihydro-4-oxobenzo[d]-1,2,3-triazin-3-ylmethyl-, S-1,2-di-(ethoxycarbonyl)ethyl-, S-6-chloro-2-oxobenzoxazolin-3-ylmethyl-, and S-2,3-dihydro-5-methoxy-2-oxo-1,3,4-thiadiazol-3-ylmethyl 0,0-di(m)ethyl phosphorodithioate;

6. phosphonates, for example, dimethyl 2,2,2-trichloro-1-hydroxyethyl phosphonate;

7. benzoylurea, for example, N-(2,6-difluorobanzoyl)-N'-(4-chlorophenyl)urea;

8. natural and synthetic pyrethroids;

9. amidines for example, N'-2-(methyl-4-chlorophenyl)-N,N-dimethyl formamidine; and 10. microbial insecticides, such as Bacillus thuringiensis.

Acaricides, for example:

1. organic tin compounds, for example, tricyclohexyl tin hydroxide and di[tri-(2-methyl-2-phenylpropyl)tin]-oxide;

2. organic halogen compounds, for example isopropyl 4,4'-dibromobenzilate, 2,2,2-trichloro-1,1-di(4-chlorophenyl)ethanol and 2,4,5,4'-tetrachlorodiphenyl sulphone; and furthermore: 3-chloro- -ethoxyimino-2,6-dimethoxybenzyl benzoate and 0,0-dimethyl S-methylcarbamoylmethyl phosphorothioate.

Fungicides, for example:

1. organic tin compounds, for example, triphenyltin hydroxide and triphenyltin acetate;

2. alkylene bisdithiocarbamates, for example, zinc ethylene bisdithiocarbamate and manganese ethylene bisdithiocarbamate;

3. 1-acyl- or 1-carbamoyl N-benzimidazole(-2) carbamates and 1,2-bis(3-alkoxycarbonyl-2-thiureido)benzene, and furthermore 2,4-dinitro-6-(2-octylphenylcrotonate), 1-[bis(dimethylamino)phosphoryl]-3-phenyl-5-amino 1,2,4-triazole, N-trichloromsthylthiophthalimide, N-trichloromethylthiotetrahydrophthalimide, N-(1,1,2,2-tetrachloroethyl-thio)tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidin-4-yl-dimethylsulphamate, 1-(4-chlorophenoxy)-3,3-dimethyl-1(1,2,4-triazol-1-yl)-2-butanone, 1-[2-(2,4-dichlorophenyl)-4-propyl-1,3-dioxolan-2-ylmethyl]-1H-1,2,4-triazole, 2,4'-difluoro-α-(1H-1,2,4-triazol-1-ylmethyl)benzhydryl alcohol, α-(2-chlorophenyl)-α(4-fluorophenyl)-5-pyrimidinemethanol, α-(2-clorophenyl)-α-(4-chlorophenyl)-5-pyrimidinemethanol, 1-(isopropylcarbamoyl)-3-(3,5-dichlorophenyl)-hydantoin, N-(1,1,2,2-tetrachloro-ethylthio)-4-cyclohexene-1,2-carboximide, N-trichloromethyl-thio-4-cyclohexene-1,2-dicarboximide, N-tridecyl-2,6-dimethylmorpholine, and 5,6-dihydro-2-methyl-1,4-oxathiine-3-carboxanilide.

The dosages of the composition according to the invention desired for practical application will, of course depend on various factors, for example, field of application, selected active substance, form of composition, nature and extent of the infection and the weather conditions. In general it holds that favourable results are achieved with a dosage which corresponds to 250–1000 g of the active substance per hectare.

When applied against phytophagous microorganisms good results are achieved when the soil is treated with a composition comprising an amount of active compound which corresponds to 2–100 kg of active substance per hectare. When applied to the seed itself, which is preferred from economical considerations, a dosage is preferred which corresponds to 100–1500 mg of active substance per kg of seed.

The new compounds of the invention can be prepared as follows.

For example, the new thio compounds of the general formula

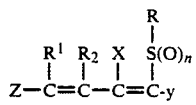

wherein

R, $R_1$, $R_2$, X, n, Y and Z have the meanings given hereinbefore, can be prepared by reacting a compound of the general formula

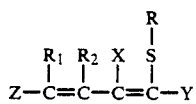

with an oxidant. Suitable oxidants are hydrogen peroxide and peroxycarboxylic acids, for example, performic acid, peracetic acid or a substituted perbenzoic acid, for example, p-nitroperbenzoic acid or m-chloroperbenzoic acid.

For the preparation of the sulphone, hydrogen peroxide is preferably used as an oxidant. When peroxycarboxylic acids are used, for example, the above-mentioned percarboxylic acids, the sulphide can be oxidized selectively to the sulphoxide. These oxidation reactions are preferably carried out in a polar organic solvent, for example, formic acid, acetic acid, a ketone, for example acetone, or a chlorinated hydrocarbon, for example, methylene chloride. The reaction temperature depends on the reagents used and the selected solvent, and may vary between $-20°$ C. and the boiling-point of the solvent, preferably between $-10°$ C. and room temperature.

After the final product has been isolated, it may be purified, if desired, by recrystallisation or column chromatography.

Thiophenes to be used for the above oxidation reaction can be prepared as follows.

Thiophenes of the general formula

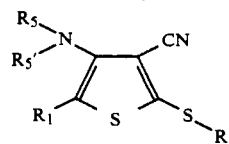

wherein

R and $R_1$ have the meanings given hereinbefore, and $R_5$ and $R'$ are equal or different and represent hydrogen atoms, $C_1$-$C_4$ alkyl groups or $C_2$-$C_5$ alkylcarbonyl groups, may be prepared by reacting a compound of the general formula

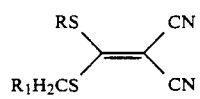

with a base, after which the amino group of the resulting compound of the general formula VI, wherein $R_5$ and $R_5'$ are hydrogen atoms, may optionally be converted with a suitable acylation agent and/or alkylation agent. A suitable base for the cyclisation reaction is an alkali metal hydride or alkali metal hydroxide, for example, NaH NaOH, or KOH. This reaction is preferably carried out in a dipolar aprotic solvent for example, DMF, at a temperature between $0°$ C. and the boiling-point of the solvent. As an alkylation agent may be used a suitable halide or a dialkyl sulphate, preferably in the same solvent preferably at slightly decreased temperature.

As an acylation agent may be used a suitable acyl halide or acid anhydride, preferably under the influence of a suitable catalyst, viz. An organic base, preferably 4-(N,N-dimethylamino)pyridine.

Starting compound VII may be prepared according to the reaction scheme:

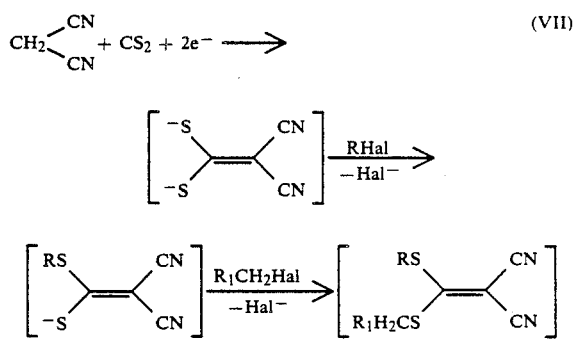

Compound (VII), well as the other intermediate products replaced in brackets, is usually not isolated but is immediately converted into the desired thiophene VI by means of a base. In the above reactions, Hal is halogen, for example, chlorine. The first reaction step is preferably car. ried out in a polar solvent, for example, a dipolar aprotic solvent, for example, DMF, at decreased temperature. In the second reaction step a suitable alkylation agent is used, for example, a halide or a dialkylsulphate, under the same reaction conditions. The third reaction step is preferably carried out in the same solvent at a temperature between $0°$ C. and the boiling-point of the solvent.

Compound VI, in which $R_5$ and $R_5'$ are hydrogen atoms, may alternatively be prepared via the following intermediate products;

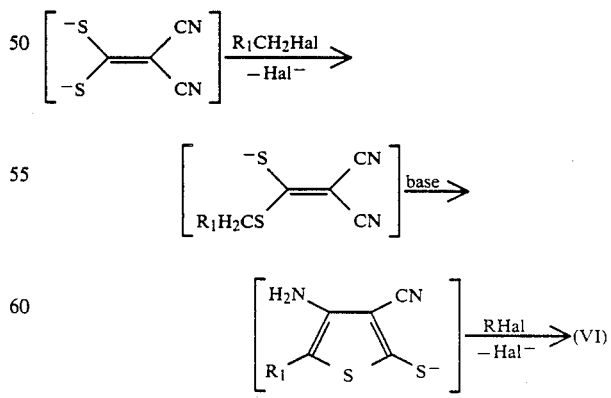

The 4-aminothiophenes thus obtained can be converted into thiophenes which are unsubstituted in the 4-position by reaction with an alkyl nitrite, preferably in a polar organic solvent, for example, a dipolar aprotic solvent, for example, DMF, preferably at elevated temperature, for example, between approximately 50° and 70° C. As an alkyl nitrite may be used, for example, isoamyl nitrite.

The above-mentioned 4-aminothiophenes can be converted into the corresponding 4-halothiophenes by reaction with an alkyl nitrite or a nitrite of an alkali metal. for example sodium or potassium in the presence of the desired halogen ions, for example. a hydrohalogenic acid or a metal halide, preferably an anhydrous cupric halide. The reaction with a nitrite of an alkali metal is prefer. ably carried out in a polar organic solvent, for example methylene chloride or acetonitrile, if desired in a two. phase system with water or a saturated saline solution. A catalyst, for example. a metal halide such as cupric chloride, may optionally be added to stimulate the latter conversion. The reaction with an alkyl nitrite is the presence of an anhydrous metal halide is preferably carried out in a polar organic solvent, like acetonitrile.

Thiophenes of the general formula

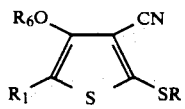

wherein R and $R_1$ have the meanings given hereinbefore, and $R_6$ is a $C_1$-$C_4$ alkyl group, may be prepared by reacting a compound of the general formula

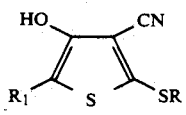

with a suitable alkylation agent, for example, an alkyl halide. This reaction is preferably carried out in a polar organic solvent, for example, acetonitrile, at a reaction temperature between 0° C. and the boiling-point of the solvent, under the influence of a suitable base, for example, $K_2CO_3$, and in the presence of a suitable amine, like triethylamine.

The 4-hydroxythiophene used as the starting compound for the last-mentioned reaction can be obtained via the following reaction scheme:

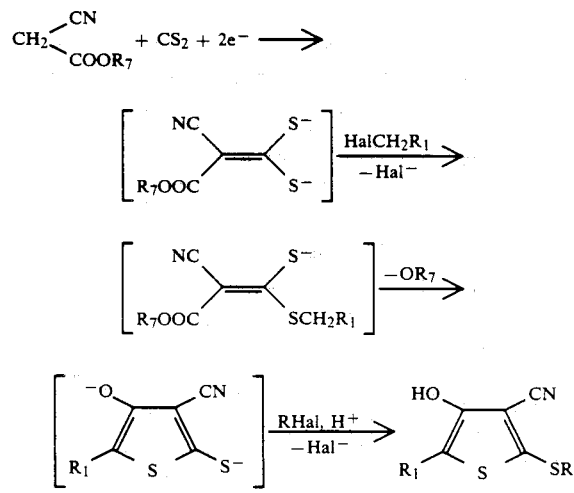

The reaction conditions do not differ from those of the corresponding reaction steps in the first reaction scheme. $R_7$ is a lower alkyl group, for example, methyl or ethyl. The alkylation in the last reaction step is carried out with a suitable alkylating agent, for example, a halide or dialkyl sulphate, preferably in a polar organic solvent, for example, DMF at slightly reduced temperature. The step preceding the alkylation is a ring closure which can be carried out under the influence of a base, for example, an alkali metal hydride or hydroxide, for example, NaH, NaOH or KOH, under the same reaction conditions.

Thiophenes of the general formula

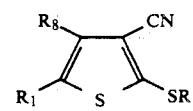

wherein R and $R_1$ have the meanings given hereinbefore, and $R_8$ is a $C_1$-$C_4$ alkyl group or a substituted or unsubstituted phenyl group, can be prepared by reacting a compound of the general formula

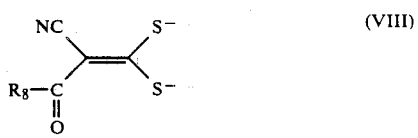 (VIII)

successively with a compound of the general formula $R_1$—$CH_2$—Hal and with a compound of the general formula RHal, wherein Hal is a halogen atom. The reactions are preferably carried out in a polar organic solvent for example, DMF, at a temperature between 0° C. and the boiling-point of the solvent.

The starting compound of the general formula VIII can be prepared by reacting $CS_2$ and a base with a compound of the general formula

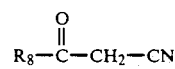

This reaction is preferably carried out in the same solvent mentioned hereinbefore at slightly reduced temperature.

Thiophenes of the general formula

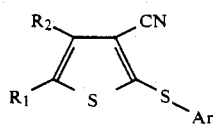

wherein $R_1$ and $R_2$ have the meanings given hereinbefore and Ar is a substituted or unsubstituted phenyl group, can best be prepared by reacting a thiophene of the general formula

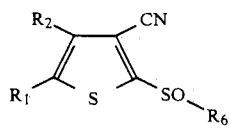

wherein the symbols have the meanings given hereinbefore, with a thiophenol of the general formula ArSH. This reaction is preferably carried out in a polar organic solvent, for example, acetonitrile, at a temperature between 0° C. and the boiling point of the solvent. If desired, a quantity of an organic base, for example, an amine like triethylamine, may stimulate the conversion.

Intermediate 3,5-diformylthiophenes can be prepared from the corresponding 3.5-dicyanothiophenes by a method as described in J. Org. Chem. 29, 3046-3049 (1964).

Intermediate 5-alkylsulphonylthiophenes can be prepared from the corresponding 5-alkoxycarbonylthiophenes by the following reaction sequence: saponification of the ester group in the 5-position to the free carboxylic acid; decarboxylation. e.g. with Cu-powder and an amine, e.g. quinoline; chlorosulfonation e.g. with chlorosulphonic acid in the presence of phosphorus pentachloride; and finally conversion of the 5-chlorosulphonyl group in an alkylsulphonyl group via reduction to the corresponding alkali metal sulphinate with an alkali metal sulphite and a base, followed by alkylation e.g. with an alkylhalide.

Intermediate 4-phenoxy- or 4-phenylthiothiophenes can be prepared by converting the corresponding 4-halothiophenes with a substituted or unsubstituted phenol or thiophenol respectively. In a corresponding manner can be prepared thiophenes substituted with an amino group forming part of a heterocyclic ring, viz. by converting the corresponding 4-halothiophene with the heterocyclic amino compound.

Intermediate compounds of the general formula

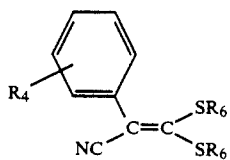

wherein the symbols have the meanings given hereinbefore, can be prepared by reacting a compound of the general formula

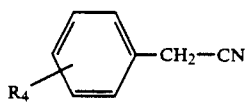

with $CS_2$ and a suitable base, for example, an alkali metal hydride like NaH, preferably in a polar organic solvent, for example, DMF, at a slightly reduced temperature, after which the resulting compound is alkylated with a suitable alkylating agent, for example, an alkyl halide of the general formula $R_6Hal$.

Intermediate benzothiophenes of the general formula

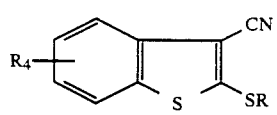

wherein R and $R_4$ have the meanings given hereinbefore, can be prepared via the following reaction scheme:

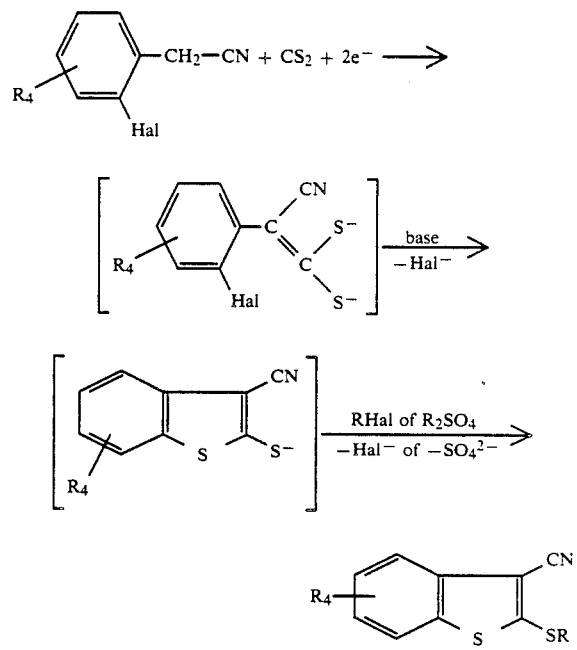

The first reaction step can be carried out by reacting the starting substance, in which Hal is a halogen atom, with $CS_2$ under the influence of a suitable base, for example, sodium hydride, preferably in a polar organic solvent, for example, DMF, at a temperature between 0° C. and the boiling point of the solvent. The subsequent reactions can be carried out in the same manner as corresponding, previously described reactions.

The inventions will now be described in greater detail with reference to the following specific examples.

EXAMPLE I

Preparation of 2-methylsulphinyl-3-cyano-5-acetylthiophene (1).

5.0 g of 83% m-chloroperbenzoic acid are gradually added while stirring at a temperature of 0°-5° C. in 45 minutes to a solution of 5.0 g of 2-methylthio-3-cyano-5-acetylthiophene in 500 ml of methylene chloride. After stirring for another 30 minutes at 5° C., a saturated solution of sodium bicarbonate in approximately 50 ml of water is added; the reaction mixture is then stirred for 60 minutes. The organic layer is separated, washed with water and dried. After distilling off the solvent, the desired product is obtained in a yield of 4.6 g; melting-point 150° C.

In a corresponding manner, in which, optionally, p-nitroperbenzoic acid is used as an oxidant and chloroform as a solvent, the following compounds are prepared:

| Comp. | Melt. point °C. (phys. char.) |
|---|---|
| (2) | 153 |
| (3) | 148 |
| (4) | 145 |
| (5) | 94 |
| (6) | 186-188 |
| (7) | 130 |
| (8) | 80 |
| (9) | 109 |
| (10) | 166 |

-continued

| Comp. | Melt. point °C. (phys. char.) |
|---|---|
| (11) | 192–195 |
| (12) | 130 |
| (13) | 100 |
| (14) | 98 |
| (15) | syrup; $R_f(CH_2Cl_2) = 0.25$ |
| (17) | 130 |
| (19) | syrup; $R_f(CH_2Cl_2) = 0.30$ |
| (20) | 115–118 |
| (23) | 74 |
| (24) | 94 (decomp) |
| (25) | 120 |
| (26) | 171–173 |
| (27) | 156–158 |
| (28) | 112–115 |
| (29) | 167–169 |
| (30) | 127,5–133,5 |
| (31) | 91–97 |
| (32) | 90–93 |
| (33) | 104–105,5 |
| (34) | 58 |
| (35) | 169–171 |
| (36) | oil: $R_f(CH_2Cl_2) = 0.20$ |
| (37) | 77–79 |
| (38) | 119 |
| (39) | 70–71 |
| (40) | 72–74 |
| (41) | 70 |
| (42) | 123–127 |
| (43) | 78–79 |
| (44) | 80–81 |
| (46) | 143–146 |
| (47) | 103–106 |
| (48) | 170–172 |
| (49) | 137–139 |
| (50) | 82–87 |
| (51) | 124–128 |
| (52) | 136.5–138 |
| (53) | oil; $R_f((C_2H_5)_2O) = 0.30$ |
| (54) | syrup; $R_f(CH_2Cl_2) = 0.22$ |
| (55) | 83 |
| (56) | 76–78 |
| (57) | 155–157 |
| (58) | 143–145 |
| (59) | 120 |
| (60) | 146–151 |
| (61) | 114–116 |
| (62) | 46–48 |
| (63) | 93–95 |
| (64) | 86–88 |
| (65) | 164–167 |
| (66) | 174–177 |
| (67) | 124–127 |
| (68) | 127–128 |
| (69) | 125–128 |
| (70) | 140–142 |
| (71) | 124–126 |
| (72) | 109–111 |
| (73) | 82–86 |
| (74) | 79–84 |
| (75) | 69–72 |
| (76) | 151 (decomp) |
| (77) | 172–174 |
| (78) | 149–151 |
| (79) | 113–115 |
| (80) | oil; $R_f(CH_2Cl_2) = 0.18$ |
| (81) | oil; $R_f(CH_2Cl_2) = 0.15$ |
| (82) | 132–135 |
| (83) | 90–92 |
| (85) | 99–101 |
| (86) | 84–86 |
| (87) | 117–119 |
| (88) | 90–92 |
| (90) | oil; $R_f(CH_2Cl_2) = 0.14$ |
| (91) | 68–73 |
| (92) | 110 |
| (93) | 84–87 |
| (94) | 94–96 |

EXAMPLE II

Preparation of 2-ethylsulphonyl 3,5-dicyanothiophene (16).

2 ml of 35% hydrogen peroxide are added to a solution of 1.62 g of 2-ethylthio-3,5-dicyanothiophene in 50 ml of aetic acid. After heating at approximately 100° C. for approximately 1 hour, another ml of 35% hydrogen peroxide is added, succeeded by heating for another hour at approximately 100° C. Upon cooling the substance crystallises out and can be sucked off. After washing with ethanol the desired compound is obtained in a yield of 1.49 g; melting-point 121°–124° C.

The following compounds are prepared in a corresponding manner:

| Compound | Melting-point °C. |
|---|---|
| (18) | 138–140 |
| (21) | 115–117 |
| (22) | 140–143 |
| (45) | 189–191 |
| (84) | 216–218 |
| (89) | 119–121 |

EXAMPLE III

Preparation of 2-methylthio-3,5-dicyano-4-aminothiophene.

A concentrated solution of 50 g of KOH in approximately 30 ml of water is slowly added dropwise to a solution of 26.5 g of malonic acid dinitrile in approximately 250 ml of dimethyl formamide to which 45 ml of carbon disulphide have been added. During the addition the mixture is stirred and kept at a temperature of 0°–10° C. by cooling. After 10 minutes, 60.0 g of methyl iodide are slowly added dropwise while stirring and cooling and then, after 30 minutes, 30.5 g of chloroacetonitrile. The cooling bath is removed and 4.0 g of powdered KOH are added, the temperature of the reaction mixture rising to approximately 42° C. After stirring for another hour at 30°–35°° C., 600 ml of water and 100 ml of diethyl ether are added, after which the formed precipitate is sucked off, washed successively with water, isopropyl alcohol and diethyl ether, and dried. The desired product is obtained in a yield of 54.5 g and sublimates at 260° C.

The following compounds are prepared in a corresponding manner:
2-ethylthio-3-cyano-4-amino-5-acetylthiophene, used for the preparation of compound (10) according to Example I.
2-methylthio-3-cyano-4-amino-5-ethoxycarbonylthiophene, used for the preparation of compound (29) according to Example I;
2-n-hexylthio-3,5-dicyano-4-aminothiophene, used for the preparation of compound (38) according to Example I;
2-ethylthio-3,5-dicyano-4-aminothiophene, used for the preparation of compound (46) according to Example I;
2-methylthio-3-cyano-4-amino-5-formylthiophene, used for the preparation of compound (48) according to Example I;
2-ethylthio-3-cyano-4-amino-5-formylthiophene, used for the preparation of compound (49) according to Example I;

2--n-propylthio-3-cyano-4-amino-5-acetylthiophene, used for the preparation of compound (57) according to Example I;
2-n-butylthio-3-cyano-4-amino-5-acetylthiophene, used for the preparation of compound (58) according to Example I;
2-ethylthio-3-cyano-4-amino-5-benzoylthiophene, used for the preparation of compound (65) according to Example I;
2-ethylthio-3-cyano-4-amino-5-(4-chlorobenzoyl)thiophene, used for the preparation of compound (66) according to Example I;
2-n-propylthio-3-cyano-4-amino-5-benzoylthiophene, used for the preparation of compound (67) according to Example I;
2-n-butylthio-3-cyano-4-amino-5-benzoylthiophene, used for the preparation of compound (88) according to Example I;
and furthermore:
2-methylthio-3-cyano-4-amino-5-acetylthiophene;
2-ethylthio-3,5-dicyano-4-aminothiophene;
2-ethylthio-3-cyano-4-amino-5-formylthiophene;
2-n-propylthio-3,5-dicyano-4-aminothiophene;
2-methylthio-3-cyano-4-amino-5-formylthiophene;
2-methylthio-3-cyano-4-amino-5-benzoylthiophene;
2-n-octylthio-3,5-dicyano-4-aminothiophene;
2-ethylthio-3-cyano-4-amino-5-ethoxycarbonylthiophene;
2-methylthio-3-cyano-4-amino-5-(4-chlorobenzoyl)thiophene;
2-n-butylthio-3,5-dicyano-4-aminothiophene;
2-n-propylthio-3-cyano-4-amino-5-(4-chlorobenzoyl)thiophene; and
2-benzylthio-3,5-dicyano-4-aminothiophene.

EXAMPLE IV (a) The thiophenes unsubstituted in the 4-position and used for the preparation of the compounds (1), (4), (8), (9), (16), (21), (28), (30), (40), (44), (47), (51), (52), (64), (73), (80), (81) and (90), mentioned in Examples I and II, are prepared as follows from the corresponding 4-aminothiophenes obtained according to Example III:

Preparation of 2-methylthio-3,5-dicyanothiophene.

20.0 g of 2-methylthio-3,5-dicyano-4-aminothiophene obtained according to Example III are added portion-wise to a solution of 20.0 g of isoamylnitrite in 300 ml of dimethyl formamide at 62° C. while stirring. At a temperature of 65°-70° C. stirring is continued for another 30 minutes and the reaction mixture is then evaporated to approximately 100 ml. After the addition of 400 ml of water, the formed precipitate is sucked off, washed successively with water, isopropanol and petroleum ether, taken up in approximately 300 ml of methylene chloride and dried. The solution is filtered over silica gel and decolorized with charcoal. After the addition of isopropanol and evaporating methylene chloride, the crystalline product is sucked off, washed successively with isopropanol and petroleum ether, and dried. The desired compound is obtained in a yield of 14.0; melting-point 117° C.

(b) The 4-halothiophenes used for the preparation of the compounds (2), (3), (5), (7), (18), (22), (31), (33), (34), (36), (37), (39), (42), (43), (50), (61), (72), (78), (79), (86), (89) and (92), mentioned in Examples I and II, are prepared as follows from the corresponding 4-aminothiophenes obtained according to Example III.

Preparation of 2-ethylthio-3,5-dicyano-4-chlorothiophene.

Cupric chloride ($CuCl_2.2H_2O$) in an amount of 100 g is dissolved in 300 ml of conc. hydrochloric acid. After addition of 2 l of acetonitrile, simultaneously a conc. solution of 60 g of sodium nitrite in water and 121.2 g of 2-ethylthio-3,5-dicyano-4-aminothiophene, obtained according to Example III, in portions are added while cooling at $-5°$ C. After stirring for an hour without external cooling the formed precipitate is sucked off and washed with acetonitrile. After evaporating the filtrate the residue is dissolved in methylene chloride and washed with water, dried, filtered and evaporated. The desired 2-ethylthio-3 5-dicyano-4-chlorothiophene can be purified by dissolving in methylene chloride and chromatographing over silica. The product can be recrystallized by evaporating methylene chloride and adding diisopropyl ether. Yield 52.66 g; melting point 93°-96° C.

Alternatively the 4-halothiophenes can be prepared as follows:

Preparation of 2-n-butylthio-3-cyano-4-chloro-5-benzoylthiophene.

Isoamyl nitrite in an amount of 15 ml is added to a mixture of 10.1 g of anhydrous $CuCl_2$ in 100 ml of dry acetonitrile, kept at a temperature of 65°-70°. While stirring a solution of 15.8 g 2-n-butylthio-3-cyano-4-amino-5-benzoylthiophene, obtained according to Example III, in 200 ml of dry acetonitrile, is added while maintaining the reaction temperature at ca. 65° C. After stirring for half an hour at 65°-70° C. and cooling down to room temperature the reaction mixture is evaporated. The residue is dissolved in methylene chloride, after which 6N hydrochloric acid is added. The methylene chloride layer is separated, washed with 6N hydrochloric acid. dried, filtered and after suppletion of isopropanol, partially evaporated The desired 2-n-butylthio-3-cyano-4-chloro-5-benzoylthiophene crystallizes out and is sucked off and dried; yield 11.85 g; melting point 78°-80° C.

(c) 2-Ethylthio-3-cyano-4-N-methylamino-5-acetylthiophene used for the preparation of compound (17) mentioned in Example I is prepared as follows from the corresponding 4-aminothiophene obtained according to Example III:

1.2 g of 55% sodium hydride are added portion-wise, while stirring, to a solution of 5.4 g of 2-ethylthio-3-cyano-4-amino-5-acetylthiophene in 100 ml of dimethyl sulphoxide. The mixture is stirred for 45 minutes, after which 2.5 ml of dimethyl sulphate are slowly added. After stirring for another hour, the reaction mixture is poured into 400 ml of water. The formed precipitate is filtered off and washed successively with water, petroleum ether, little isopropanol and again petroleum ether. After recrystallisation from isopropanol, 2-ethylthio-3-cyano-4-N-merhylamino-5-acetylthiophene is obtained in a yield of 2.73 g.

(d) 2---Ethylthio-3,5-dicyano-4-(N-acetyl-N-methylamino)-thiophene, used for the preparation of compound (54) mentioned in Example I, is prepared as follows from the corresponding 4-aminothiophene obtained according to Example III:

To a suspension of 21 g of 2-ethylthio-3,5-dicyano-4-aminothiophene, 3 g of 4-(N,N-dimethylamino)pyridine and 20 ml of triethylamine in 300 ml of acetonitrile, stirred at 50° C., is added dropwise 18 g of acetic acid anhydride. After evaporation and taking up the residue in diethylether, containing 5% acetic acid, the precipitate is sucked off, washed successively with water, isopropanol, diethylether, toluene and diethylether again, and dried. The 4-N-acetylamino compound is obtained in a quantity of 16 g. To a mixture of 16 g of the last-mentioned compound and 12 g of $K_2CO_3$ in 300 ml of acetonitrile is added 20 g of methyl iodide. The reaction mixture is stirred and refluxed for 5 hours, during which period 3 portions of approx. 12 g of methyl iodide are added. The liquid is decanted and the solid is washed with acetonitrile and methylene chloride successively. The total filtrate is evaporated to dryness and taken up into methylene chloride. After the addition of isopropanol, decolorizing with charcoal and evaporating methylene chloride, 2-ethylthio-3,5-dicyano-4-(N-acetyl-N-methylamino)thiophene is obtained in a yield of 9 g; melting point 68° C.

EXAMPLE V

2-Methylthio-3,5-diformylthiophene, used for the preparation of compound (70) mentioned in Example I, is prepared as follows:

To a suspension of 7.20 g of 2-methylthio-3,5-dicyanothiophene, obtained according to Example IV (a), in 120 ml of dry toluene is added, while stirring and under a nitrogen blanket, 75 ml of a 20% solution of diisobutyl aluminumhydride in toluene. The reaction mixture is stirred for two hours, after which 12 ml of methanol is added under cooling in ice. The reaction mixture is stirred in ice plus conc. sulphuric acid till a clear solution. The toluene phase is separated and the water phase washed twice with toluene. The combined organic phase is washed with water, dried, filtered and evaporated. The residue is recrystallized from ethanol yielding 2-methylthio-3,5-diformylthiophene in a quantity of 3.0 g; melting point 135°-137° C.

In a corresponding way 2-ethylthio-3,5-diformyl-4-chlorothiophene, used for the preparation of compound (83) mentioned in Example I, is prepared from 2-ethylthio-3,5-dicyano-4-chlorothiophene, obtained according to Example IV (b).

EXAMPLE VI (a) Preparation of 2-methylthio-3,5-dicyano-4-hydroxythiophene.

A cold, highly concentrated solution of 25 g of KOH in approximately 15 ml of water is slowly added dropwise to a solution of 20.0 g of cyanoacetic acid methyl ester and 18.0 g of carbon disulphide in approximately 300 ml of dimethyl formamide while stirring and cooling to below approximately 0° C. After stirring for another 20 minutes, a solution of 15.5 g of chloroacetonitrile in 10 ml of acetonitrile is added dropwise to the reaction mixture at −5° C. to 0° C. After stirring for another 30 minutes, a highly concentrated solution of 13 g of KOH in water is added and stirred for 30 minutes at 40° C. Then 29 g of methyl iodide are added dropwise and, after 30 minutes, 25 ml of concentrated hydrochloric acid. After concentration of the reaction mixture under reduced pressure to approximately 300 ml, approximately 600 ml of water are added. The resulting precipitate is sucked off, washed successively with water, little isopropanol and di-isopropyl ether, and dried. The desired product is obtained in a yield of 19.0 g; the substance decomposes above 200° C.

The following compounds are prepared in a corresponding manner:
2-ethylthio-3,5-dicyano-4-hydroxythiophene,
2-ethylthio-3-cyano-4-hydroxy-5-acetylthiophene,
2-propargylthio-3,5-dicyano-4-hydroxythiophene,
2-methylthio-3-cyano-4-hydroxy-5-acetylthiophene.
2-n-butylthio-3,5-dicyano-4-hydroxythiophene,
2-n-propylthio-3,5-dicyano-4-hydroxythiophene,
2-methylthio-3-cyano-4-hydroxy-5-benzoylthiophene,
2-n-propylthio-3-cyano-4-hydroxy-5-benzoylthiophene, and
2-ethylthio-3-cyano-4-hydroxy-5-(4-chlorobenzoyl)thiophene.

(b) From the compounds obtained according to Example VI (a), the 4-alkoxythiophenes used for the preparation of compounds (12), (13), (14), (23), (24), (25), (41), (55), (59), (74), (75) and (76),mentioned in Example I, are prepared as follows:

Preparation of 2-methylthio-3,5-dicyano-4-methoxythiophene.

6 g of 2-methylthio-3,5-dicyano-4-hydroxythiophene 10 ml of methyl iodide, 10 g of potassium carbonate, and 3 ml of triethylamine are refluxed in 300 ml of acetonitrile while stirring. After 2 hours the reaction mixture is filtered warm and evaporated to dryness. The residue is taken up in 200 ml of methylene chloride and washed successively with a solution of potassium carbonate in water and with water. The methylene chloride solution is then dried and evaporated to dryness. After recrystallisation of the residue from isopropanol, the desired product is obtained in a yield of 4.0 g; melting-point 132° C.

EXAMPLE VII

Preparation of 2-ethylthio-3-cyano-4-methyl-5-acetylthiophene.

To a suspension of 10.5 g of sodium salt of cyanoacetone in 200 ml of dimethylformamide 9.0 ml of carbon disulphide are gradually added while stirring cooling in ice and keeping under nitrogen, succeeded by 4.5 g of sodium hydride dispersion. After stirring for an hour with cooling, 8.4 ml of chloroacetone are added dropwise under the same reaction conditions. After stirring for another hour, 0.4 g of powdered NaOH are added and finally, after again stirring for another 0.5 hour, 8.0 ml of ethyl iodide under the same conditions. After stirring, the reaction mixture for again another hour and leaving to stand overnight it is poured 1 l of ice water and extracted with diethyl ether. The organic phase is washed with water three times, dried, treated with charcoal, filtered and evaporated. After recrystallisation from isopropanol, the residue yields the desired product in a yield of 9.54 g; melting-point 51°-52° C.

In a corresponding way other 4-alkyl substituted thiophenes are prepared, starting substances for the preparation of compounds (56), (62), (63) and (91) according to Example I.

2-Methylthio-3-cyano-4-(4-chlorophenyl)-5-acetylthiophene, starting substance for the preparation of compound (6) according to Example I, is prepared in a corresponding way, in which, however, in the first reaction step dimethyl sulphoxide is used instead of dimethyl formamide as a solvent.

In a corresponding way other 4-aryl substituted thiophenes are prepared. starting substances for the preparation of compounds (26), (35), (71) and (87) according to Example I.

EXAMPLE VIII

Preparation of
2-ethylthio-3-cyano-6-chlorobenzothiophene, starting substance for the preparation of compound (20) according to Example I.

3.62 ml of carbon disulphide are added while stirring, cooling in cold water and keeping under nitrogen to a solution of 7.44 g of 2.4-dichlorophenyl acetonitrile in 80 ml of dry dimethyl formamide, succeeded by the gradual addition of 3.6 g of a sodium hydride dispersion. After stirring for an hour, 3.20 ml of ethyl iodide are added dropwise under the same reaction conditions. The reaction mixture is stirred for another hour at room temperature and then 24 hours at 100° C. After cooling and pouring into ice water, the formed precipitate is sucked off, washed successively with water and petroleum ether, and recrystallised from ethanol. The desired product is obtained in a yield of 3.89 g; melting-point 91°–93° C.

The following compounds are prepared in a corresponding manner:

2-methylthio-3-cyano-4-chlorobenzothiophene. starting substance for the preparation of compound (11) according to Example I, and 2-ethylthio-3-cyano-6-nitrobenzothiophene, starting substance for the preparation of compound (27) according to Example I.

EXAMPLE IX

The preparation of α-cyano-β,β-bis(methylthio)-3,4-dichlorostyrene, starting substance for the preparation of compound (15) according to Example I, and α-cyano-β,β-bis(methylthio)-4-chlorostyrene, starting substance for the preparation of compound (19) according to Example I, as well as the starting substances for the preparation of compounds (53) and (93) according to Example I, is carried out as described by Chauhan et al. in Tetrahedron 1976, 32 (14), p. 1779.

EXAMPLE X

Preparation of 2-phenylthio-3,5-dicyanothiophene,
starting substance for the preparation of compound (32) according to Example I and of compound (45) according to Example II.

4.4 ml of thiophenol and 5.0 ml of triethylamine are added, while stirring, to a solution of 8.9 g of 2-ethylsulphinyl-3,5-dicyanothiophene, obtained according to Example I, in 100 ml of acetonitrile. After leaving to stand overnight, the reaction mixture is refluxed for 8 hours. After evaporating the solvent, the residue is taken up in methylene chloride and chromatographed over a 1 l dry silica gel column. The desired product is obtained in a yield of 9.07 g; melting-point 68°–71° C. Optionally, any 2-alkylsulphinyl compound may be used as the starting substance.

The following compound is prepared in a corresponding manner:

2-phenylthio-3,5-dicyano-4-chlorothiophene, starting substance for the preparation of compound (82) according to Example I.

EXAMPLE XI

Preparation of
2-methylthio-3-cyano-5-methylsulphonylthiophene, starting substance for the preparation of compound (60) according to Example I.

To a solution of 4.36 g of 2-methylthio-3-cyano-5-ethoxycarbonylthiophene, obtained according to Example IV (a), in 40 ml of dioxane, is added while stirring 40 ml of 2N NaOH. After stirring for two hours the reaction mixture is acidified with 45 ml 2N Hcl. The precipitated 5-carboxythiophene compound is sucked off, washed with water and recrystallized from acetonitrile; yield 3.01 g; melting point 230°–234° C. This 5-carboxythiophene compound in an amount of 1.99 g together with 4 ml of quinoline and 0.4 g of Cu-powder is heated on 200° C. during approx. 15 minutes. After cooling down, diethylether, water and 20 ml 2N Hcl are added. The ether phase is separated off, washed with water, dried, decolorized with charcoal, filtered and evaporated. 2-Methylthio-3-cyanothiophene is obtained in a yield of 0.92 g as an oil; $R_f(CH_2Cl_2)=0.45$. The reaction is repeated with larger quantities. The last product in an amount of 6.98 g is added dropwise to a mixture of 7.1 ml of $ClSO_3H$ and 8.9 g of $Pcl_5$ under stirring and cooling to below 20° C. After stirring for half an hour at room temperature, the mixture is poured on ice. The formed precipitate is sucked off, washed with water and dissolved in methylene chloride. After drying, decolorizing with charcoal, filtration, adding diisopropylether and evaporating methylene chloride, the desired 2-methylthio-3-cyano-5-chlorosulphonylthiophene precipitates in an amount of 7.60 g; melting point 112°–115° C. The above chlorosulphonyl compound is converted to the corresponding methylsulphonyl compound via the corresponding sodium sulphinate by adding 7.50 g to 7.6 g of $Na_2SO_3$ and 10.1 g of $NaHCO_3$ in 60 ml of water. While stirring the reaction mixture is warmed slowly up to 70° C. and stirred at 70° C. for half an hour. To the solution obtained 3.75 ml of methyl iodide is added; reflux for 5 hours. After evaporating the volatile components in vacuo, the formed precipitate is sucked off, washed with water and recrystallized from methanol. 2-Methylthio-3-cyano-5-methylsulphonylthiophene is obtained in a yield of 2.88 g; melting point 126°–128° C.

In a corresponding way is prepared 2-ethylthio-3-cyano-4-chloro-5-methylsulphonylthiophene, starting compound for the preparation of compound (77) according to Example I and of compound (84) according to Example II.

EXAMPLE XII

Preparation of
2-ethylthio-3,5-dicyano-4-phenoxythiophene, starting substance for the preparation of compound (94) according to Example I.

Phenol in an amount of 2.82 g is dissolved in 30 ml of methanol comprising 0.69 g of sodium. After adding 50 ml of dimethylformamide the methanol is evaporated. The residual solution is added while stirring to a solution of 6.86 g of 2-ethylthio-3,5-dicyano 4 -chlorothiophene, obtained according to Example IV (b), in 40 ml of dimethylformamide. After stirring for one hour, the reaction mixture is poured on 0.5 l of ice water. The formed precipitate is sucked off, washed with water and dissolved in methylene chloride. The solution is washed with a bicarbonate solution, dried, filtered, supplied with diisopropylether and evaporated partially. The crystallized 2-ethylthio-3,5-dicyano-4-phenoxythiophene is sucked off; yield 5.78 g; melting point 111°–112° C.

In a corresponding way 2-methylthio-3,5-dicyano-4-phenylthio-thiophene, starting substance for the preparation of compound (85) according to Example I, is prepared.

EXAMPLE XIII

Preparation of 2-ethylthio-3,5-dicyano-4-(1,2,4-triazol-1-yl)thiophene, starting substance for the preparation of compound (68) according to Example I.

Sodium in an amount of 0.69 g is dissolved in 30 ml of methanol. After adding 30 ml of dimethylformamide the methanol is evaporated and 2.07 g of 1,2,4-triazole in 30 ml of dimethylformamide is added. Under stirring and flushing with nitrogen the mixture is refluxed for 1.5 hours. After cooling in ice/acetone a solution of 6.86 g of 2-ethylthio-3,5-dicyano-4-chlorothiophene, obtained according to Example IV (b), in 40 ml of dimethylformamide is added and the reaction mixture is stirred overnight. After pouring out in 0.5 l of ice-water the formed precipitate is sucked off washed with water and dissolved in methylene chloride. The organic phase is dried, decolorized with charcoal, filtered, partially evaporated and supplied with diisopropyl ether. The desired 2-ethylthio-3,5-dicyano-4-(1,2,4-triazol-1-yl)thiophene precipitate is sucked off, washed with diisopropyl ether and dried; yield 4.30 g; melting point 148°–151° C.

In a corresponding way 2-ethylthio-3,5-dicyano-4-(imidazol-1-yl)thiophene, starting substance for the preparation of compound (69) according to Example I, is prepared.

EXAMPLE XVI (a) Preparation of a solution of an active substance, viz. 2-methylsulphinyl-3-cyano-5-acetylthiophene (1), in a water-miscible liquid ("liquid").

10 g of the above active substance are dissolved in a mixture of 10 ml of isophorone and approx. 70 ml of dimethylformamide, after which polyoxyethylene glycol ricinyl ether as an emulsifier is added in a quantity of 10 g.

The other active substances are processed in a corresponding manner to 10 or 20% "liquids".

In a corresponding manner, "liquids" are obtained in N-methyl pyrrolidone, dimethyl formamide, and a mixture of N-methyl pyrrolidone and isophorone as solvents.

(b) Preparation of a solution of the active substance in an organic solvent.

200 mg of the active substance to be investigated are dissolved in 1,000 ml of acetone in the presence of 1.6 g of nonylphenol polyoxyethylene. After pouring in water, this solution can be used as a spraying liquid.

(c) Preparation of an emulsifiable concentrate of the active substance.

10 g of the active substance to be investigated are dissolved in a mixture of 15 ml of isophorone and 70 ml of xylene; 5 g of a mixture of a polyoxyethylene sorbitan ester and an alkylbenzene sulphonate are added to this solution as an emulsifier.

(d) Preparation of a dispersible powder (W.P.) of the active substance.

25 g of the active substance to be investigated are mixed with 68 g of kaolin in the presence of 2 g of sodium butyl naphthalene sulphonate and 5 g of lignine sulphonate.

(e) Preparation of a suspension concentrate (flowable) of the active substance.

A mixture of 10 g of active substance, 2 g of lignine sulphonate, and 0.8 g of sodium alkyl sulphate is supplied with water to a total quantity of 100 ml.

(f) Preparation of a granule of the active substance.

7.5 g of active substance, 5 g of sulphite lye, and 87.5 g of ground dolomite are mixed, after which the resulting mixture is processed to a granular composition by means of the so-called compacting method.

EXAMPLE XV

Test with respect to the protection of seedlings against a plant pathogenic seed fungus, namely *Fusarium culmorum*, by means of a seed treatment.

Wheat seed, infested with *Fusarium culmorum*, is treated with the substance to be tested in the form of a composition in a quantity of 3 g per kg of seed. The composition is obtained by pulverising the substance to be tested and then intimately mixing with kaolin in a concentration of 10% by weight. The seed thus treated is sown in a tray containing soil which is placed in a Wisconsin tank with a bottom temperature of 8°–12° C. After three weeks the number of emerged and healthy plants is determined. The emergence of healthy plants from untreated seed serves as control. For comparison, the known substances 2-methylsulphinyl-4-methyl-5-nitrothiazole (a), 2-methylsulphinyl-3-nitrothiophene (b) and 2-ethylsulphinyl-3-nitro-5-acetylthiophene (c) mentioned hereinbefore are also tested. The results are recorded in Table A below. In the examples, the numbers of the compounds refer to the specification.

TABLE A

| Compound No. | Percentage of emerged, healthy plants |
|---|---|
| (1) | 91 |
| (2) | 87 |
| (3) | 91 |
| (4) | 90 |
| (5) | 85 |
| (7) | 98 |
| (8) | 92 |
| (9) | 85 |
| (10) | 98 |
| (12) | 93 |
| (13) | 90 |
| (14) | 87 |
| (27) | 96 |
| (a), known | 68 |
| (b), known | 75 |
| (c), known | 74 |
| untreated | 67 |

EXAMPLE XVI

Test with respect to the protection of seedlings against a plant-pathogenic soil fungus, namely Pythium spp., by means of a seed treatment.

The compounds to be tested are processed to compositions by pulverising them and then mixing them intimately with kaolin in the desired concentration (see Table B). Beet seed is treated with these compositions in a quantity of 6 g of composition per kg of seed and then sown in trays with soil which was seriously infested with Pythium spp. After 3 weeks in a glass-house at 18°-22° C. and a relative humidity of 70-100%, the percentage of non-emerged and diseased seedlings (damping-off) is determined. The results are recorded in Table B. For comparison, the known substance 2-methylsulphinyl-4-methyl-5-nitrothiazole (a) is also tested.

TABLE B

| Compound No. | Dosage in mg of active substance per kg of seed | percentage damping-off |
| --- | --- | --- |
| (1) | 600 | 8 |
|  | 1200 | 7 |
| (2) | 600 | 7 |
|  | 1200 | 6 |
| (3) | 600 | 6 |
|  | 1200 | 5 |
| (4) | 600 | 10 |
|  | 1200 | 9 |
| (5) | 600 | 21 |
|  | 1200 | 17 |
| (7) | 600 | 17 |
|  | 1200 | 17 |
| (8) | 600 | 16 |
|  | 1200 | 12 |
| (9) | 600 | 15 |
|  | 1200 | 11 |
| (10) | 600 | 10 |
|  | 1200 | 9 |
| (12) | 600 | 0 |
|  | 1200 | 0 |
| (13) | 600 | 3 |
|  | 1200 | 1 |
| (14) | 600 | 23 |
|  | 1200 | 20 |
| (27) | 600 | 4 |
|  | 1200 | 2 |
| (a), known | 600 | 57 |
|  | 1200 | 45 |
| untreated | — | 72 |

EXAMPLE XVII

Toxicity with respect to warm-blooded living beings.

Lethal dose

The $LD_{50}$ is determined by orally administering the substance to be tested to male mice and determining the acute mortality. In Table C below, the $LD_{50}$ is recorded in mg/kg of body weight.

For comparison, the known compound (b) (see EXAMPLE XV) is also tested.

TABLE C

| Compound No. | $LD_{50}$ (mg/kg) |
| --- | --- |
| (7) | 400 |
| (8) | 119 |
| (10) | 141 |
| (13) | 130 |
| (33) | 246 |
| (43) | 246 |

TABLE C-continued

| Compound No. | $LD_{50}$ (mg/kg) |
| --- | --- |
| (b), known | 31.6 |

EXAMPLE XVIII

Toxicity with respect to warm-blooded living beings.

The mutagenity is determined by means of the so-called Ames test. The Ames test is carried out under the conventional standard conditions on the *Salmonella typhimurium* strain TA 100, both without metabolic activation (−S9) and with metabolic activation (+S9). The results are recorded in Table D. For comparison, the known compound (c) (see EXAMPLE XV) is also tested.

TABLE D

| Compound No. | Ames Test −S9 | +S9 |
| --- | --- | --- |
| (5) | — | — |
| (7) | — | — |
| (8) | — | — |
| (9) | — | — |
| (10) | — | — |
| (12) | — | — |
| (13) | — | — |
| (23) | — | — |
| (40) | — | — |
| (44) | — | — |
| (c), known | + | + |

EXAMPLE XIX

In vitro test on activity against *Pyrenophora graminea*.

The compound to be tested is processed in a culture medium consisting of 1% by weight of glucose, 0.2% by weight of a yeast extract (marmite), 0.5% by weight of a protein (pepton), 2.5% by weight of agar-agar, and 95.8% by weight of water, in petri dishes in concentrations of 3 and 10 ppm. The petri dishes are inoculated with the plant-pathogenic fungus *Pyrenophora graminea* and then kept at a temperature of 20° C. After 48 hours the growth-inhibiting activity of the compounds is determined visually. For comparison, the known substance (b) (see EXAMPLE XV) is also tested. The results are recorded in Table E.

TABLE E

| Compound No. | Concentration in ppm | % growth inhibition of the fungus |
| --- | --- | --- |
| (2) | 3 | 64 |
|  | 10 | 79 |
| (3) | 3 | 57 |
|  | 10 | 80 |
| (4) | 3 | 66 |
|  | 10 | 84 |
| (5) | 3 | 54 |
|  | 10 | 89 |
| (6) | 3 | 54 |
|  | 10 | 77 |
| (7) | 3 | 59 |
|  | 10 | 83 |
| (8) | 3 | 49 |
|  | 10 | 72 |
| (31) | 10 | 77 |
| (33) | 10 | 83 |
| (35) | 10 | 76 |
| (39) | 10 | 81 |
| (43) | 10 | 72 |
| (47) | 10 | 74 |
| (51) | 10 | 71 |
| (52) | 10 | 71 |

TABLE E-continued

| Compound No. | Concentration in ppm | % growth inhibition of the fungus |
|---|---|---|
| (53) | 10 | 83 |
| (66) | 10 | 84 |
| (72) | 10 | 70 |
| (78) | 10 | 86 |
| (79) | 10 | 80 |
| (82) | 10 | 80 |
| (85) | 10 | 73 |
| (86) | 10 | 76 |
| (94) | 10 | 70 |
| (b), known | 3 | 0 |
|  | 10 | 37 |
| control | — | 0 |

EXAMPLE XX

Compounds according to the invention are tested on *Fusarium culmorum* in the same manner as described in EXAMPLE XIX. The following compounds cause at least 75% growth inhibition of the fungus in a concentration of 30 ppm: (2), (3), (5), (7), (11), (12), (13), (14), (19), (22), (23), (27), (29), (31), (32), (33), (34), (35), (36), (37), (38), (39), (40), (41), (42), (43), (44), (45), (47), (51), (52), (53), (55), (57), (58), (61), (62), (64), (65), (67), (71), (72), (73), (74), (75), (78), (79), (80), (81), (82), (85), (86), (87), (88), (89), (90), (91), (92), and (93).

EXAMPLE XXI

Compounds according to the invention are tested on i Leptosphaeria nodorum in the same manner as described in EXAMPLE XIX. The following compounds cause at least 85% growth inhibition of the fungus in a concentration of 30 ppm: (2), (3), (4), (5), (7), (9), (10), (12), (13), (14), (15), (17), (19), (20), (23), (27), (31), (32), (33), (34), (35), (36) (37) (40), (41), (42), (43), (44), (45), (47), (51), (53), (58), (63), (64), (65), (67), (71), (72), (73), (74), (75) (76), (85), (86), (87), (88), (89), (92) and (94).

EXAMPLE XXII

Compounds according to the invention are tested on *Pythium splendens* in the same manner as described in EXAMPLE XIX. The following compounds cause at least 95% growth inhibition of the fungus in a concentration of 10 ppm: (1), (2), (3), (4), (5), (6), (7), (8), (9), (10), (12), (13), (14), (15), (16), {17), (18), (19), (21), (22), (25), (26), (27), (28), (30), (31), (32), (33), (34), (35), (36), (39), (40), (41), (42), (43), (45), (46), (47), (48), (49), (50), (51), (52), (54), (55), (56), (57), (58), (59), (60), (61), (66), (67), (68), (69), (70), (72), (74), (77), (78), (79), (80), (82), (83), (84), (85), (86), (89), (93) and (94).

EXAMPLE XXIII

Compounds according to the invention are tested on *Rhizoctonia solani* in the same manner as described in EXAMPLE XIX. The following compounds cause at least 75% growth inhibition of the fungus in a concentration of 30 ppm: (2), (3), (4), (15), (19), (27), (33), (34), (36), (39), (42), (43), (52), (80) and (85),

We claim:

1. Compounds of the formula

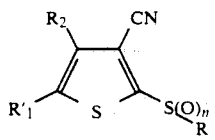

wherein
R$_1'$ is a cyano group, a formyl group, an alkylcarbonyl group having 2-5 carbon atoms or a benzoyl group which may be substituted with one or more substituents selected from the group consisting of halogen, nitro, C$_1$-C$_4$ alkyl, C$_1$-C$_4$ alkoxy, C$_1$-C$_4$ haloalkyl and C$_1$-C$_4$ haloalkoxy;

R is an alkyl group substituted or not substituted with halogen and having 1-12 carbon atoms, an alkenyl or alkynyl group having 2-4 carbon atoms, an alkadienyl group having 3 or 4 carbon atoms, or a phenyl or phenyl (C$_1$-C$_4$) alkyl group, which groups are unsubstituted or substituted with a substituent selected from halogen, nitro, cyano, C$_1$-C$_4$ alkyl, C$_1$-C$_4$ haloalkyl, C$_1$-C$_4$ alkoxy, C$_1$-C$_4$ haloalkoxy and C$_1$-C$_4$ alkylsulphonyl;

R$_2$ is a hydrogen atom, a halogen atom, an amino group unsubstituted or substituted with one or two groups selected from C$_1$-C$_4$ alkyl and C$_2$-C$_5$ alkylcarbonyl, an alkyl or alkoxy group having 1-4 carbon atoms and optionally substituted with halogen or C$_2$-C$_5$ alkylcarbonyl, or a phenyl, phenoxy or phenylthio group, which groups are unsubstituted or substituted with a substituent selected from halogen, nitro, cyano, C$_1$-C$_4$ alkyl, C$_1$-C$_4$ haloalkyl, C$_1$-C$_4$ alkoxy, C$_1$-C$_4$ haloalkoxy and C$_1$-C$_4$ alkylsulphonyl; and n is 1 or 2.

2. Compounds as claimed in claim 1 of the formula

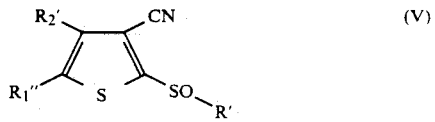

wherein
R' is an alkyl group having 1-4 carbon atoms,
R$_1''$ is a cyano group, a formyl group, an acetyl group, an unsubstituted benzoyl group or a benzoyl group substituted with one or two halogen atoms, and
R$_2'$ is a hydrogen atom, a halogen atom, an alkyl group or alkoxy group having 1 or 2 carbon atoms, or an amino group substituted or not substituted with a methyl group.

3. A fungicidal and/or bactericidal composition, characterized in that the composition, in addition to a liquid or solid carrier material, comprises a compound of the formula IV, wherein the symbols have the meanings given in claim 1.

4. A composition for the treatment of soil or seed against phytophagous micro-organisms, characterized in that the composition, in addition to a liquid or solid carrier material, comprises a compound of the formula IV, wherein the symbols have the meanings given in claim 1.

5. A composition as claimed in claim 3 or 4, characterized in that the active constituent is a compound of the formula

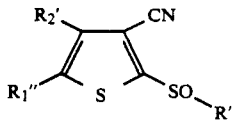 (V)

wherein

R′ is an alkyl group having 1–4 carbon atoms;

R$_1''$ is a cyano group, a formyl group, an acetyl group, an unsubstituted benzoyl group or a benzoyl group substituted with one or two halogen atoms, and R$_2'$ is a hydrogen atom, a halogen atom, an alkyl group or alkoxy group having 1 or 2 carbon atoms, or an amino group substituted or not substituted with a methyl group.

6. A method of preventing or controlling fungus infections in agriculture and horticulture, characterized in that the infested crop or the crop to be protected is treated with a composition as claimed in claim 3, in a dosage of from 250 to 1,000 g of active substance per hectare.

7. A method of preventing infections by phytophagous micro-organisms in agriculture and horticulture, characterized in that the soil destined for sowing or planting is treated with a composition as claimed in claim 4 in a dosage of from 2 to 100 kg of active substance per hectare, or that the seed, prior to sowing, is treated with a composition as claimed in claim 4 in a dosage of from 100 to 1,500 mg of active substance per kg of seed.

* * * * *